(12) United States Patent
Wittmann

(10) Patent No.: US 7,658,749 B2
(45) Date of Patent: Feb. 9, 2010

(54) METHOD FOR CREATING A TEMPORARY HYPOBARIC WOUND SPACE IN AN INTENTIONALLY LEFT OPEN SURGICAL WOUND TO DIAGNOSE SUBSTRATE LOSSES AND PREVENT EXOGENOUS CONTAMINATION WITH MICROORGANISMS

(76) Inventor: Dietmar H. Wittmann, 990 Gulf Winds Way, Nokomis, FL (US) 34275

( * ) Notice: Subject to any disclaimer, the term of this patent is extended or adjusted under 35 U.S.C. 154(b) by 198 days.

(21) Appl. No.: 11/161,817

(22) Filed: Aug. 17, 2005

(65) Prior Publication Data

US 2005/0273066 A1 Dec. 8, 2005

Related U.S. Application Data

(62) Division of application No. 09/947,070, filed on Sep. 5, 2001, now abandoned, and a division of application No. 10/636,728, filed on Jul. 13, 2004.

(51) Int. Cl.
*A61B 17/08* (2006.01)
*A61B 17/04* (2006.01)

(52) U.S. Cl. ............................. 606/215; 606/313
(58) Field of Classification Search .......... 606/213, 606/214, 215, 216, 218; 128/897
See application file for complete search history.

(56) References Cited

U.S. PATENT DOCUMENTS 4,112,947 A 9/1978 Nehring .................. 604/30

(Continued)

OTHER PUBLICATIONS

A. L. Valenta, Using the Vacuum Dressing Alternative for Difficult Wounds, American Journal of Nursing, Apr. 1994, p. 44-45.

(Continued)

*Primary Examiner*—Vy Q Bui
(74) *Attorney, Agent, or Firm*—Frijouf, Rust & Pyle, P.A.

(57) ABSTRACT

A hypobaric wound space is provided for prophylactic and diagnostic purposes in surgical wounds of the abdomen deliberately left open. The hypobaric wound space provided is established by a combination of an impermeable folio sheet or thin flexible membrane, tissue fluid absorbing gauze or sponge, a drain tube, and a suction device to create hypobaric conditions and prevent wound contamination and infection, and to collect wound fluid to diagnose protein, fluid and other substrate losses on a quantity and quality basis. More specifically the invention provided relates to postoperatively applying negative pressure to the wound space of any surgical wound that was deliberately left open by filling the wound space with medical gauze or any material that is capable of absorbing tissue fluid, sealing the wound space with an impermeable folio or flexible membrane by engaging the folio to the skin of surrounding wound edges, and evacuating air and tissue fluid from the wound space by continuous suction through a drain tube to protect the wound from contamination and infection, and to diagnose fluid and losses substrate losses on a quantity and quality basis.

5 Claims, 2 Drawing Sheets

U.S. PATENT DOCUMENTS

| | | | |
|---|---|---|---|
| 4,382,441 A | 5/1983 | Svedman | 604/291 |
| 4,452,245 A | 6/1984 | Usher | 606/151 |
| 4,569,674 A | 2/1986 | Philips et al. | 604/119 |
| 4,655,754 A | 4/1987 | Richmons et al. | 604/323 |
| 4,969,880 A | 11/1990 | Zamierowski | 604/305 |
| 5,636,643 A | 6/1997 | Argenta et al. | 128/897 |
| 5,645,081 A | 7/1997 | Argenta et al. | 128/897 |
| 5,893,368 A | 4/1999 | Sugerman | |
| 6,039,741 A | 3/2000 | Meislin | |
| 6,071,304 A | 6/2000 | Augustine et al. | 607/96 |
| 6,203,563 B1 * | 3/2001 | Fernandez | 606/215 |
| 6,725,794 B2 | 4/2004 | Usa | |
| 6,752,794 B2 | 6/2004 | Lockwood et al. | 604/313 |
| 6,855,135 B2 | 2/2005 | Lockwood et al. | 604/313 |

OTHER PUBLICATIONS

M.G. Dunlop et la., Vacuum Drainage of Groin Wounds After Vascular Surgery: a controlled trial, Br. J. Surg. May 1990, p. 562-583, vol. 77.

J.W.Saunders, Negative Pressure Device for Controlled Hypotension During Surgical Operations, The Lancet, Jun. 1952, p. 1286-1287.

D.H.Wittmann et al., The Abdominal Compartment Syndrome, Journal of the American College of Surgeons, Jun. 1995, p. 745-753, vol. 180.

P.R.Miller et al., Late Fascial Closure in Lieu of Ventral Hernia, The Journal of Trauma, Nov. 2002, p. 843-849, vol. 53 No. 5.

* cited by examiner

METHOD FOR CREATING A TEMPORARY HYPOBARIC WOUND SPACE IN AN INTENTIONALLY LEFT OPEN SURGICAL WOUND TO DIAGNOSE SUBSTRATE LOSSES AND PREVENT EXOGENOUS CONTAMINATION WITH MICROORGANISMS

This divisional application is in response to office action filed on 31 Oct. 2002 requiring "Election/Restriction" required under 35 U.S.C. 121 for claims 9-11 classified in class 606 subclass 216, of application Ser. No. 09/947,070 filed Sep. 5, 2001 and titled "Prosthesis for abdominal surgery" Class/Subclass 606/215 and "Expressively Abandoned During Examination" in favor of Continuation-in-part of application Ser. No. 10/636,728 filed Jul. 7, 2004 with the title "Prosthesis and method for lowering abdominal pressure" Class/Subclass 606/213, currently "docketed for examination". Priority is claimed based on provisional patent application No. 0/230,202 filed Sep. 5, 2000.

The present invention relates to contamination and infection prophylaxis of surgical wounds of the abdomen that were deliberately left open and removing wound fluid continuously for diagnostic purpose by creating a hypobaric space with a combination of three elements of biocompatible material termed hypobaric wound shield (HBS) or Hypopack. The Hypopack consists of three elements of biocompatible material:

(1) (Element one) An impermeable folio or plastic drape or other impermeable fabric or flexible membrane having a side that is or may be rendered adhesive covering the entire wound and engaging onto the surrounding skin for sealing the wound space off the environment.

(2) (Element two) Surgical gauze or sponge or sponge-like material that is capable of absorbing wound fluid.

(3) (Element three) wide lumen drainage tube of sufficient wall rigidity to prevent collapse under negative pressure produced by an attached suction pump with manometer.

More particularly, this invention relates to applying continuous negative pressure to an open surgical abdominal wound by sealing the wound with an impermeable folio with adhesive properties on one side and engaging the folio to the skin of surrounding wound edges and evacuating air from the wound space by continuous suction to protect the wound from contamination and uncontrolled fluid losses.

Definition List 1

| Term | Definition |
| --- | --- |
| Hypobar | A pressure below normal atmospheric pressure. |
| Hypobaric wound shield (HBS) | A combination of three elements of biocompatible material that produces and maintains a negative pressure in an open surgical wound, which prevents contamination of the wound and that allows for measuring of body fluid losses. |
| Hypopack | Short name for HBS. |
| Open wound | Any surgical wound that could not be closed and/or was deliberately left open with or without the fascia separated. |
| Element one | an impermeable folio or plastic drape or other impermeable fabric having a side that is or may be rendered adhesive to cover the entire wound and to engage onto the surrounding skin for sealing the wound space from the environment. |
| Adhesive | Any substance that is used to bond two surfaces together. |
| Element two | Any surgical gauze or sponge or sponge-like material that is capable of absorbing wound fluid and that may or may not have antimicrobial and/or antiviral or wound healing enhancing properties. |
| Element three | Any drainage tube with a lumen sufficiently large to transport body fluids, that is made of any biocompatible material and that has sufficient wall rigidity to prevent collapse under negative pressure up to −200 mm Hg. |
| Lumen | The hollow part of a tube. |
| Abdominal hypertension | Increase of intra abdominal pressure above normal physiological levels. |
| Compliance | The potential of a structure such as the fascia to expand. |
| Organ system | The various organ structures of the body that function in concord. |
| Infusion bag | A bag made of biocompatible plastic material attached to a small tube that is used to add external fluids and nutrition into the vascular system. |
| Fistula | An open communication between a physiological or pathological hollow structure of the body with another such structure or the skin. |
| Visceral edema | Swelling of the visceral or intra-abdominal organs. |
| Omentum | An apron-like structure of loose connective tissue and immunologically competent cells that normally lays on top of the intestines beneath the abdominal wall. |
| Epigastrium | Small area on the anterior abdominal wall and inferior to the costal margins of the anterior chest wall. |
| Rectus muscle | Longitudinal segmented muscle lateral to the abdominal midline that is enfolded in the abdominal fascia. |
| Axillae | Plural of axilla. |
| Fascial expander prosthesis | Any mesh or fabric that is used to bridge the fascia gap in case of fascial dehiscence. |
| Manometer | A device to measure pressure. |
| Laparotomy | Surgical opening of the abdominal cavity. |
| Surgical wound | Wound that is created by a surgical incision as opposed to traumatic wound that is created by non surgical trauma. |
| Vacuum | A space absolutely devoid of matter. |
| Substrate | The base on which an organism lives |

A number of prior art references emphasize the value of hypobaric wound dressings or the provision of hypobaric pressure in the space above the surface of chronic wounds. Often the term vacuum is inaccurately used in prior art, because it is not possible to create a true vacuum in a wound. A true vacuum would be incompatible with cell survival because the fragile cellular wall structure would burst from the pressure difference between intracellular pressure and a vacuum with virtually no pressure at all. The following recent U.S. patents deal with the nature of devices that can create hypobaric conditions for enhancing wound treatment: U.S. Pat. Nos. 6,855,135, 6,725,794, 6,071,304, 5,645,081, 5,636,643, 4,969,880, 4,655,754, 4,569,674, 4,382,441, and 4,112,947. All of such references are incorporated herein by reference for purposes of disclosing the nature of such hypobaric treatment of wounds which is different from the present invention where the hypobaric conditions created are not meant to enhance healing of the wound directly. The paper of Valenta, A. in "American Journal of Nursing. April 1994. "Using the Vacuum Dressing Alternative for Difficult Wounds" provides an insight into the claims of prior art to improve wound healing. The Hypopack is not used for treatment to enhance wound healing. Instead, the Hypopack is used for prophylaxis of contamination and infection and diagnosis of fluid and substrate losses on a quantity and quality basis from the abdominal cavity by temporarily covering a wound that was purposefully left open by the surgeon until said wound can be closed permanently, usually after three to eight days.

U.S. Pat. Nos. 6,855,135 and 6,725,794 were filed on May 13, 2002 and Nov. 27, 2001 respectively. Said two most recent patents discuss in detail all prior art that claims beneficiary healing effect of providing a "vacuum" in the space above the wound to promote healing in chronic wounds. The present invention deals with acute wounds exclusively and does not claim to promote wound healing.

U.S. Pat. Nos. 5,645,081 and 5,636,643 disclose a method of treating tissue damage by applying negative pressure to a wound sufficient duration and magnitude to promote tissue migration and thus facilitate closure of the wound. FIG. 1 of U.S. Pat. No. 5,645,081 discloses an open cell polyester foam section covering the wound, a flexible hollow tube inserted into the foam section at one end and attached to a vacuum pump at another end, an adhesive sheet overlying the foam section and tubing to adhere to the skin surrounding the wound in order to form a seal that allows the creation of a "vacuum" when the suction pump is operating. The present invention is different because it does no claim to promote tissue migration and wound healing. In other prior art similar systems are describe for the purpose of irrigating a wound (U.S. Pat. Nos. 4,382,441 and 4,112,947). The present invention is not used to irrigate the wound.

The present invention is intended to be used in circumstances that force a surgeon to leave open an abdominal wound. Said wounds are primarily sterile and subject to contamination with exogenous microorganisms. Said wounds are also subject to uncontrolled fluid losses, and losses of essential vital substrates. Contamination of open wounds may lead to life threatening infection. Uncontrolled fluid losses may deplete the patient's proteins. Physiological protein balance is essential for wound healing. If this balance is upset due to uncontrolled losses, the substitution of proteins becomes an important factor in wound healing and survival.

Circumstances that force a surgeon to leave a wound open may come about, for example, in abdominal compartment syndrome that occurs when intra-abdominal pressure rises acutely, because the abdominal cavity with its content is contained within an envelope of limited compliance. Increasing intra-abdominal volume, as seen with inflammatory edema, translates directly into pressure increases and, beyond a certain threshold, strangulates blood flow to all structures within the envelope.

Abdominal compartment syndrome impairs functions of vital organ systems in humans and animals. With sustained abdominal hypertension above a critical value, high mortality rates are observed.

When blood flow is diminished cells do not receive sufficient substrates and oxygen that is essential for generating energy to sustain life. Cellular death may lead to sequential organ system dysfunction and, if not treated, to death.

The first publication about renal function impairment in the presence of abdominal hypertension was published in 1876, by E C Wendt (Arch. Heilkunde. 1876; 17:527). Clinicians, however, did not appreciate the condition for a century and only recently began treating abdominal hypertension by leaving the abdomen open with the fascias separated or temporarily covering the fascial defect over exposed organs with any fabric including infusion bags and meshes as described in U.S. Pat. No. 4,452,245 (Schein, et al, J Am College of Surgeons 180:745-753, 1995). Sugerman developed an external device to treat increased intra-abdominal pressure (U.S. Pat. No. 5,893,368).

Leaving the abdomen open, however, is associated with high mortality rates, fistula formation, and large incisional hernias. All wounds left open become infected. The use of available meshes (U.S. Pat. No. 4,452,245) to bridge the gap between fascias is associated with similarly high infection and mortality rates.

With all methods the open wound is exposed and subject to exogenous infection that may foster said detrimental events leading to organ system dysfunction and death. In a recent publication the open abdomen technique is advocated as the treatment of choice for abdominal compartment syndrome. (Miller, P R, J. Trauma 53:843-849, November 2002) The authors observed high intra-abdominal pressure and abdominal compartment syndrome from visceral edema in 122 of 646 patients who underwent laparotomy for trauma, and the abdomen of these 122 patients was left open after incising the fascia. More than 40% died, by and large of infection.

There is obviously a need for a method that temporarily covers the wound and prevents exogenous contamination of any surgical wound that cannot be closed at the end of a surgical intervention. Exogenous contamination may be prevented by protecting the open wound with an impermeable folio cover sealed to the adjacent skin and creating hypobaric conditions within the wound space by applying negative pressure through a tube that not only evacuates air from the wound space but also any wound fluid losses, which provides diagnostic information that will help to determine how much fluid, protein and other substrate must be replaced or substituted.

Figure 1:
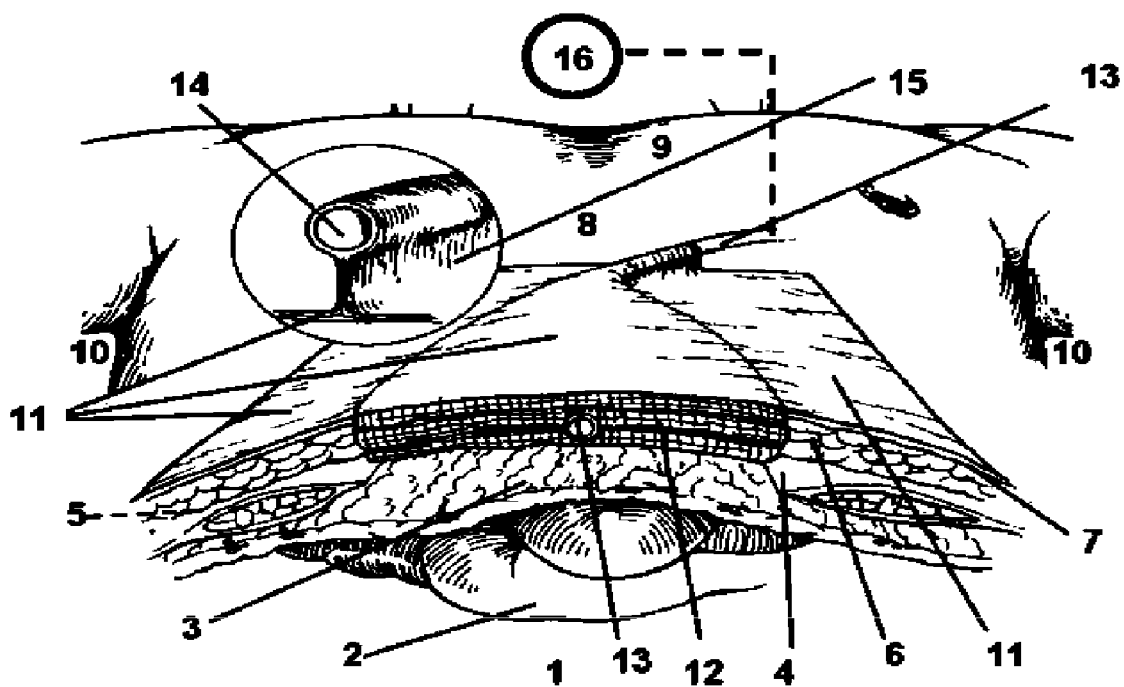
FIG. 1 shows the anterior abdominal cavity and anterior abdominal and chest wall with an open abdominal wound and dehiscent fascia that is covered with the present invention, the Hypopack depicting its three elements in place in an open wound to show the relation of element one, the impermeable folio or flexible membrane 11, element two the fluid absorbing material 12, and element three the drain tube 13.
Figure 2:
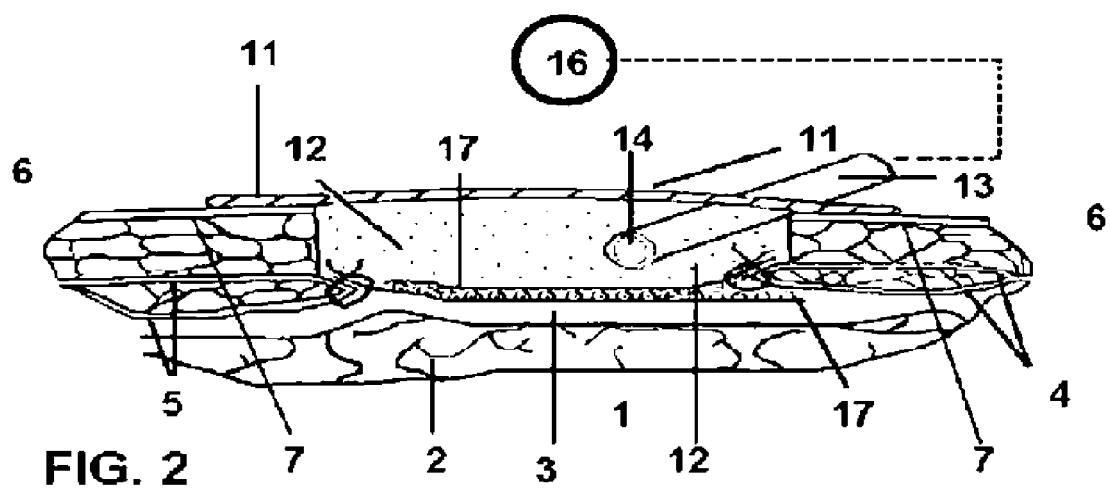
FIG. 2 is a cross section of a wound that is covered by a hypobaric wound shield and where the space between the fascial borders has been bridged with a synthetic mesh.

Numbers in the FIGS. 1 and 2 have the following meaning:

(1) Abdominal Cavity (1)
(2) Intestines (2)
(3) Omentum (3)
(4) Fascia left side (4)
(5) Abdominal rectus muscle and surrounding fascia, right side (5)
(6) Subcutaneous tissue (6)
(7) Skin (7)
(8) Epigastrium (8) (not shown on FIG. 2)
(9) Chest wall (9) (not shown on FIG. 2)
(10) Axillae (10) (not shown on FIG. 2)

(11) Impermeable drape or folio (element one of the Invention) (11)
(12) Gauze or body fluid absorbing material/sponges (element two of the invention) (12)
(13) Drain tube (element three of the invention) (13)
(14) Lumen of drain tube (14)
(15) Mesentery of folio to seal drain conduit (15) (not shown on FIG. 2)
(16) Suction device e.g. a suction pump with manometer (16)
(17) Mesh or fascial expander prosthesis (17) (not shown on FIG. 1)

DESCRIPTION OF PREFERRED EMBODIMENT

The preferred embodiment of the invention includes the three elements of the invention in a sealed outer package with a sterile interior such as a transparent plastic bag for storage until use.

The preferred method of using the device or implant of the present invention is shown with the help of illustrations FIGS. 1 and 2. When a surgeon desires to protect an operative incision that was intentionally left open from becoming contaminated the hypobaric would shield may be formed by doing the following:

Any surgical wound that was left open in general or any open abdomen in particular as shown in FIGS. 1 and 2 may be covered by using the hypobaric wound shield. This is accomplished by packing element one (gauze or any body fluid absorbing sponge/material) 12 into the wound space between the fascias 3 and subcutaneous tissue 4 up to the level of the skin 5. A suction drain tube (element three) 13 and 14 is imbedded into element one 12. An impermeable folio, such as a plastic drape (element two) 11 having an adhesive side is engaged onto the skin to cover the entire wound and surrounding skin, and creating an airtight tunnel 15 for the drain tube. This seals the abdominal cavity and keeps it sterile. The area of the skin that is covered by the impermeable folio, such as a plastic drape 11, should cover a distance sufficiently large to prevent communication (leaks) between skin and folio and thereby preventing communication (leaks) between wound and environment. Air and wound fluid are immediately removed from the wound space by connecting the lumen 14 of the drain tube 13 to a suction device (pump) that is capable of producing hypobaric conditions with negative pressure up to −100 mm Hg. Additionally, the suction device may be connected to a container to collect wound fluid for measurement of protein losses and other factors for possible replacement.

The hypobaric wound shield must be replaced when negative pressure cannot be maintained any longer. This may happen accidentally or intentionally during wound inspection.

All materials used must be biocompatible and sterile before use All components of the hypobaric wound shield are packaged in an internally sterile package such as a transparent plastic bag for storage until use.

REFERENCES CITED

Besides the U.S. patents cited relevant references are cited below.
1. Dunlop et al., Br. J. Surg., 77: 562-563, 1990, "Vacuum drainage of groin wounds after vascular surgery: a controlled trial".
2. Fleischmann, W. Wund Forum Spezial. IHW '94. "Vakuumversiegelung zur Behandlung von Problemwunden" (with English translation: Vacuum Sealing for Treatment of Problematical Wounds.
3. Saunders, J. W., The Lancet, pp. 1286-1287, Jun. 28, 1952, "Negative-Pressure Device for Controlled Hypotension During Surgical Operations"
4. Schein, M. et al., Journal Am College of Surgeons 180: 745-753, 1995, "The abdominal compartment syndrome: the physiological and clinical consequences of elevated intra-abdominal pressure.
5. Valenta, A., American Journal of Nursing. April 1994. "Using the Vacuum Dressing Alternative for Difficult Wounds."
6. Wendt, E. C., Archiv Heilkunde, Vol. 17, p. 527-527, 1876. "Über den Einfluss des intraabdominellen Druckes auf die Absonderungsgeschwindigkeit des Harnes."

What is claimed is:

1. A hypobaric wound shield for temporarily hermetically sealing an open surgical wound, the open surgical wound traversing through a skin layer and a fascia layer to expose an abdominal organ within a abdominal cavity, the open surgical wound defining a first skin side and a second skin side of the skin layer and a first fascia side and a second fascia side of the fascia layer, the partitioning of the first skin side with the second skin side and the first fascia side and the second fascia side define a wound space, the hypobaric wound shield comprising:
   a fluid absorbing material positioning within the wound space for absorbing a wound fluid;
   a flexible impermeable shield having an adhesive side and a non-adhesive side;
   said adhesive side of said flexible impermeable shield securing to the first skin side and the second skin side for sealing the open surgical wound;
   a drain tube extending between an input lumen and an output lumen for displacing said wound fluid;
   a mesentery in said flexible impermeable shield for sealing said drain tube and guiding said drain tube from the wound space through said flexible impermeable shield; and
   a vacuum device coupling to said output lumen of said drain tube for producing a negative pressure within the wound space.

2. A hypobaric wound shield for temporarily hermetically sealing an open surgical wound as set forth in claim 1, wherein said fluid absorbing material includes a surgical gauze.

3. A hypobaric wound shield for temporarily hermetically sealing an open surgical wound as set forth in claim 1, wherein said fluid absorbing material includes a sponge.

4. A hypobaric wound shield for temporarily hermetically sealing an open surgical wound as set forth in claim 1, wherein said flexible impermeable shield includes a polymeric drape.

5. A hypobaric wound shield for temporarily hermetically sealing an open surgical wound as set forth in claim 1, wherein a mesh is secured between the first fascial side and the second fascial side of said fascia layer; and
   said mesh having a plurality of voids for permitting said wound fluid to traverse from the abdominal cavity to the wound space.

* * * * *